United States Patent [19]
Lin

[11] Patent Number: 5,330,474
[45] Date of Patent: Jul. 19, 1994

[54] VERTEBRAL LOCKING AND RETRIEVING SYSTEM

[76] Inventor: Chih-I Lin, 513 S. Golden Pardos Dr., Diamond Bar, Calif. 10765

[21] Appl. No.: 98,859

[22] Filed: Jul. 29, 1993

Related U.S. Application Data

[63] Continuation-in-part of Ser. No. 935,271, Aug. 26, 1992, Pat. No. 5,257,994, which is a continuation-in-part of Ser. No. 924,448, Aug. 4, 1992, Pat. No. 5,196,014.

[51] Int. Cl.$^5$ .............................................. A61B 17/58
[52] U.S. Cl. ......................................... 606/61; 606/60; 606/54
[58] Field of Search ...................... 606/53, 54, 55, 57, 606/59, 60, 61, 72, 73, 86, 87, 90, 105

[56] References Cited

U.S. PATENT DOCUMENTS

| | | | |
|---|---|---|---|
| 3,997,138 | 12/1976 | Crock et al. ...................... | 606/61 X |
| 4,611,580 | 9/1986 | Wu ..................................... | 606/73 X |
| 4,854,304 | 8/1989 | Zielke ................................ | 606/61 |
| 4,988,349 | 1/1991 | Pennig .............................. | 606/57 X |
| 5,030,220 | 7/1991 | Howland ........................... | 606/61 |
| 5,047,029 | 9/1991 | Aebi et al. ........................ | 606/61 |
| 5,053,034 | 10/1991 | Olerud .............................. | 606/61 |

*Primary Examiner*—Robert A. Hafer
*Assistant Examiner*—Sam Rimell
*Attorney, Agent, or Firm*—Bacon & Thomas

[57] ABSTRACT

A vertebral locking and retrieving system comprising a locking pin, a connector, a locking component, a coupling component, a remedial component, and securing components is disclosed. The locking pin includes a threaded end and a locking end. The threaded end is adapted to be secured to a normal, healthy vertebra. The connector comprises a through hole and an integrally formed cubic portion at one lateral side of the through hole. The cubic portion has a locking aperture adapted to non-rotatably accept the locking end of the locking pin. The locking component is engaged with the locking end of the locking pin after it has passed through the locking aperture of the cubic portion to hold the connector onto the locking pin. The coupling component is threadably connected one end thereof to the through hole of the connector. The remedial component is secured at one end thereof to a deformed vertebra immediately adjacent to the healthy vertebra to which the locking pin is secured or a vertebra next to the deformed vertebra and different from this healthy vertebra and is connected at its other end thereof to the other end of the coupling component. The securing components enable the remedial component to be fixedly secured to the coupling component.

8 Claims, 5 Drawing Sheets

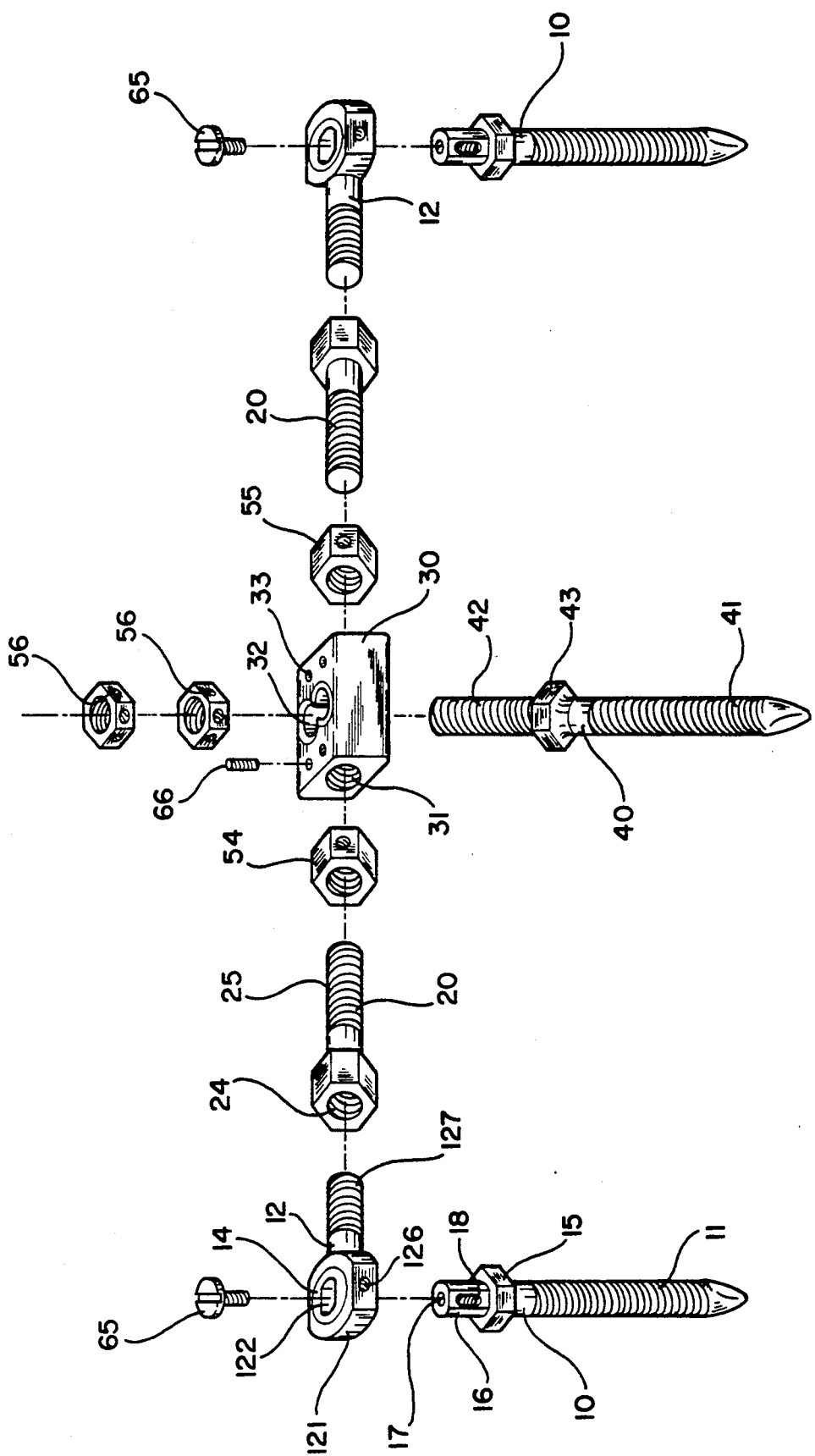

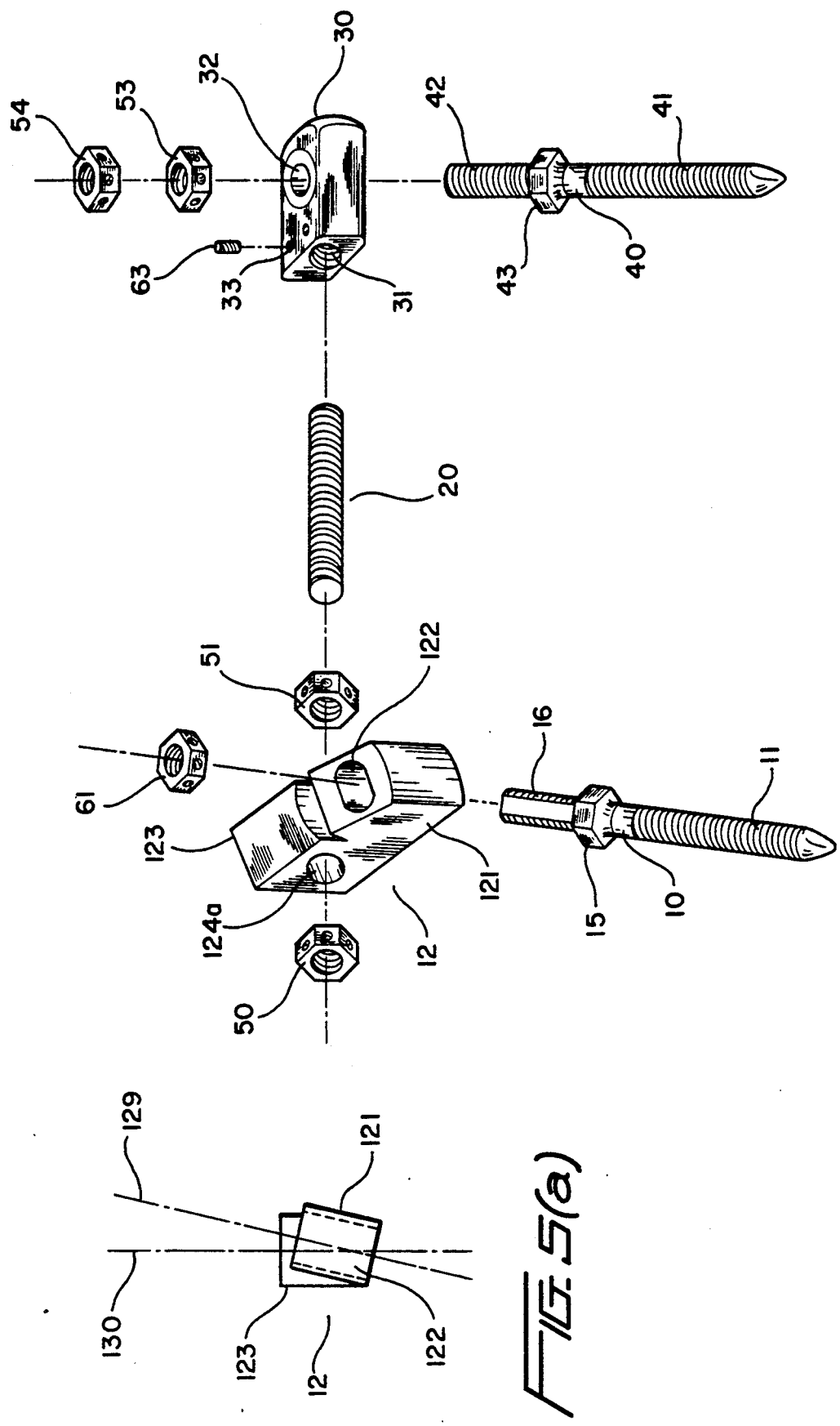

VERTEBRAL LOCKING AND RETRIEVING SYSTEM

This is a continuation in part of U.S. application Ser. No. 07/935,271 filed Aug. 26, 1992, which is a continuation in part of U.S. Pat. No. 5,196,014 and has been allowed by the U.S. Patent and Trademark Office.

BACKGROUND OF THE INVENTION

1. Field of the Invention

The present invention relates to a vertebral locking and retrieving system.

2. Description of the Prior Art

In general, conventional vertebral locking and retrieving systems of the prior art involve a locking process of multiple vertebrae, as exemplified by the LUGUE rod and the HARRINGTON rod, both made by Zimmer Company of U.S.A., and the ROY-CAMILLE plate produced by Howmedia Corporation of U.S.A. Such known prior art arrangements require a surgeon to make a long incision, which generally takes up too much of a surgeon's time and may bring about excessive bleeding by a patient receiving the treatment. The case in point is the LUGUE rod, which must be secured to two upper and lower vertebrae immediately adjacent to the injured or the deformed vertebra. This means that a surgeon is required to make a large incision to fix at least five segments of the spinal column. As a result, the patient's ability to move about is greatly hampered in the wake of such a surgical operation. In addition, the pressure exerting on the patient's nervous system by the locking and retrieving system of the prior art can not be effectively mitigated in view of the facts that the locking process is confined to a rear plate and that the retrieval of a front plate is not possible.

Furthermore, the surgical implantation of the conventional vertebral locking and retrieving systems of the prior art is further complicated by the fact that seven cervical vertebrae, twelve thoracic vertebrae, five lumbar vertebrae, and one caudal vertebra of the human spinal column differ in curvatures.

Other types of prior art vertebral locking and retrieving systems are disclosed respectively in U.S. Pat. Nos. 4,611,581 and 4,696,290. Such systems have also failed to deal with the surgical problems described above. In short, the existing vertebral locking and retrieving systems of the prior art have failed to address the surgical problems that are derived mainly from the fact that the curvatures of various vertebrae of the human spinal column are different from one another.

It is therefore the primary object of the present invention to provide a vertebral locking and retrieving system with a locking pin and a connector, in which said locking pin and/or said connecor are designed in such unique manners that they have specific angles permitting the locking pin to cooperate with the specific curvatures of various vertebrae and that they serve to overcome the problems during and after the surgical operation having to do with locking multiple vertebrae.

It is another object of the present invention to provide a vertebral locking and retrieving system with means which can be used to lock two vertebrae of the spinal column.

It is still another object of the present invention to provide a vertebral locking and retrieving system with a locking pin and a connector, in which said locking pin and/or said connector are designed to have specific angles for correcting the position of various vertebrae having different curvatures.

SUMMARY OF THE INVENTION

In order to achieve the objects of the present invention, a vertebral locking and retrieving system comprising a locking pin, a connector, a locking component, a coupling component, a remedial component, and a plurality of securing components is disclosed. The locking pin includes a threaded end, a locking end and a stopping protrusion located between the threaded end and the locking end, in which the threaded end defines a first longitudinal axis and is adapted to be secured to a normal, healthy vertebra. The connector comprises a receiver part having a through hole and an integrally formed substantially cubic portion at one lateral side of the through hole. The cubic portion has a locking aperture adapted to non-rotatably accept the locking end of the locking pin such that the cubic portion rests on the stopping protrusion to prevent movement of the cubic portion towards the vertebra. The locking component is engaged with the locking end of the locking pin after it has passed through the locking aperture of the cubic portion to hold the connector onto the locking pin. The coupling component is extended into the through hole of the receiver part and threadably attached to the receiver part at one end thereof. The remedial component is secured at one end thereof to a deformed vertebra immediately adjacent to the healthy vertebra to which the locking pin is secured or a vertebra next to the deformed vertebra and different from this healthy vertebra and is connected at its other end thereof to the other end of the coupling component. The securing components enable the remedial component to be fixedly secured to the coupling component. Furthermore, the locking end of the locking pin is formed an acute angle of deflection relative to the first longitudinal axis and/or the cubic portion of the connector is formed with a longitudinal axis defined by the locking aperture at an acute angle of deflection relative to an extending plane perpendicular to a longitudinal axis defined by the through hole of the receiver part.

The remedial component of the present invention may be a conventional screw, a laminar hook, or a locking pin with a specified angle. A plurality of remedial components may be used in combination with one coupling component of the present invention depending on the position and the symptom of the deformed vertebra and the surgical requirements.

In the preferred arrangement, the coupling components used in the present invention may include a single threaded rod or a plurality of threaded rods joined as a one-piece component by blocks having threaded bores into which the rods are received.

The foregoing features, objectives and advantages of the present invention will be better understood by studying the following detailed description of the preferred embodiments, in conjunction with the drawings provided herein.

BRIEF DESCRIPTION OF THE DRAWINGS

FIG. 4 shows an exploded perspective view of a locking and retrieving system constructed according to a fourth preferred embodiment of the present invention.

FIG. 5 shows an exploded perspective view of a locking and retrieving system constructed according to a fifth preferred embodiment of the present invention.

FIG. 5(a) shows a front view of the connector 12 in FIG. 4.

DETAILED DESCRIPTION OF THE PREFERRED EMBODIMENTS

In general, the vertebral locking and retrieving system of the present invention can be made of orthopedic materials, such as the iron-based stainless steel 316LVM, the titanium-based material Ti-6-4, and an alloy of chromium, molybdenum and cobalt. The number of locking pins is of course dependent on the surgical requirements, as well as the connectors. The vertebral locking and retrieving system of the present invention is characterized in that the locking end and the threaded end of the locking pin form a specified angle and/or the internally threaded bore or the externally threaded portion and the plate of the connector form a specified angle, such as 180°, 175°, 170°, or 165°, with a respective deflection plane angle being 0°, 5°, 10°, 15°, so as to meet the angular requirements of various vertebrae. Furthermore, with the employment of different combination of the locking pin and connector assemblies having the above-mentioned deflection plane angles of 0°, 5°, 10°, 15°, a slipped veertebrae can be properly retrieved to have an appropriate angle consistent with normal human anatomy, such as 0°, 5°, 10°, 15°, 20° (5°+15°), 25° (10°+15°), and 30° (15°+15°). This is something beyond the reach of the prior art systems. In addition, working with the prior art system, a surgeon would have to depend entirely on his or her own judgment and clinical experiences to determine the locking angle of the deformed vertebra. On the other hand, the present invention permits a surgeon to study in advance, before operating on the patient, the X-ray negatives with regard to the locking angles of the patient's vertebrae so as to select the most suitable locking pin and the connector to use.

Moreover, the locking pin and the connector of the present system are two separated components such that the connector can be fastened to the locking pin after the locking pin being secured to a vertebra, and thus permits the surgeon to have a chance to amend the locking angle by choosing a connector having a different deflection angle if the locking pin secured to the vertebra should deflect from its planned angle.

Figure 1:
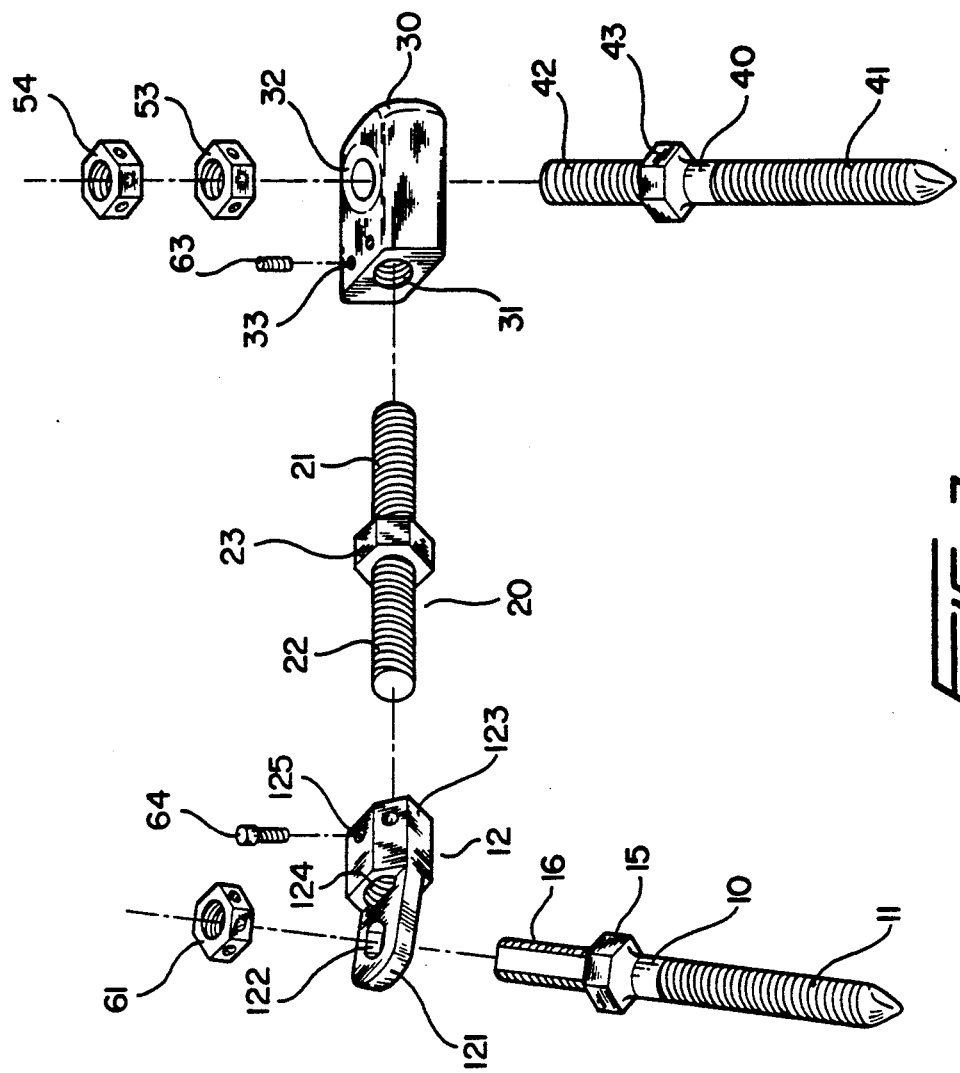
FIG. 1 shows an exploded perspective view illustrating a vertebral locking and retrieving system constructed according to one of the preferred embodiments of the present invention.
Figure 1A:
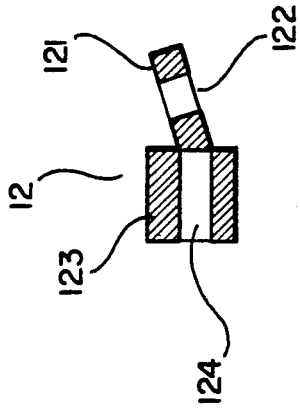
FIG. 1(a) is a longitudinal vertical sectional view of the connector 12 of the vertebral locking and retrieving system of FIG. 1.

Referring to FIGS. 1 and 1(a), the vertebral locking and retrieving system embodied in the present invention is shown comprising mainly a locking pin 10, a connector 12, a threaded rod 20, a block 30, a remedial screw 40, and a plurality of nuts 61, 53 and 54.

The locking pin 10 has a threaded end 11 at its lower end which is used to lock the normal vertebra immediately adjacent to the deformed vertebra under treatment. Another end defines a rectangular or similar shaped post having a threaded locking end 16. Near the locking end 16 there is formed a stopping protrusion 15. The connector 12 includes a receiver part 123 at one end thereof and an integrally formed plate 121 at the other end thereof. The receiver part 123 has an internally threaded bore 124, and the plate 121 has an aperture 122 adapted to non-rotatably accept the locking end 16 such that the plate 121 rests on the stopping protrusion 15 to prevent movement of the plate 121 towards the vertebra. The nut 61 is then engaged with the locking end 16 to fix the plate 121 onto the locking end 16 of the locking pin 10. As shown in FIG. 1(a), the plate 121 of the connector is formed at an acute angle of deflection relative to a longitudinal axis defined by the internally threaded bore 124.

The block 30 is provided with a through hole 32, a plurality of small threaded holes 33, and a large threaded bore 31. The remedial screw 40 comprises a screw end 41 intended to be secured to the deformed vertebra, a threaded end 42 to be placed through the through hole 32 of the block 30, and a stopping protrusion 43, located between the screw end 41 and the threaded end 42, intended for use in stopping the block 30.

The threaded rod 20 has a right-handed thread 21 at one end, a left-handed thread 22 at the other end, and polygonal drive portion 23 at the center thereof. The right-handed thread 21 is used to engage with the large threaded bore 31 of the block 30, the left-handed thread 22 is used to engage with the internally threaded bore 124 of the connector 12, and the polygonal drive portion 23 is for connecting to a spanner. Due to the right- and left-handed threads being provided at two ends of the threaded rod 20, the connector 12 and the block 30 can be mounted on the two ends of threaded rod 20 and moved towards each other as the threaded rod 20 is rotated.

The block 30 and the remedial screw 40 are fastened securely by means of nuts 53 and 54. If necessary, additional reinforcing screws 64 may be provided to secure the engagement between the connector 12 and threaded rod 20 by tightening the reinforcing screws 64 into screw holes 125 of the connector 12 and against the threaded rod 20. Similarly, additional reinforcing screws 63 may be provided to secure the engagement between the block 30 and threaded rod 20 by tightening the reinforcing screws 63 into screw holes 33 of the block 30 and against the threaded rod 20.

A similar vertebral locking and retrieving system which is useful in correcting and restoring a slipped vertebra of the lumber vertebrae is disclosed in the FIGS. 1, and 2(a)-2(c) of the present inventor's U.S. Pat. No. 5,196,014, the disclosure of which is incorporated herein by reference.

Figure 1B:
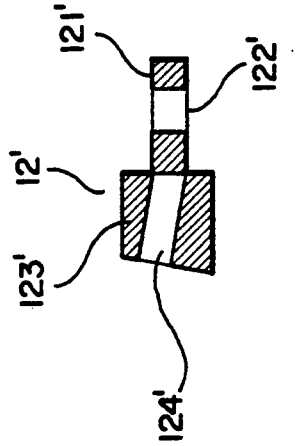
FIG. 1(b) is a longitudinal vertical sectional view of a connector 12' which can be used to replace the connector 12 of the vertebral locking and retrieving system shown in FIG. 1.

It is obvious that a connector 12' shown in FIG. 1(b) can be used to replace the connector 12 of the system described in the present FIG. 1 and still has the same function. In FIG. 1(b) the numerals with apostrophes are used to designate parts or structures corresponding to those having like numerals without apostrophes in the above described embodiment.

Figure 2:
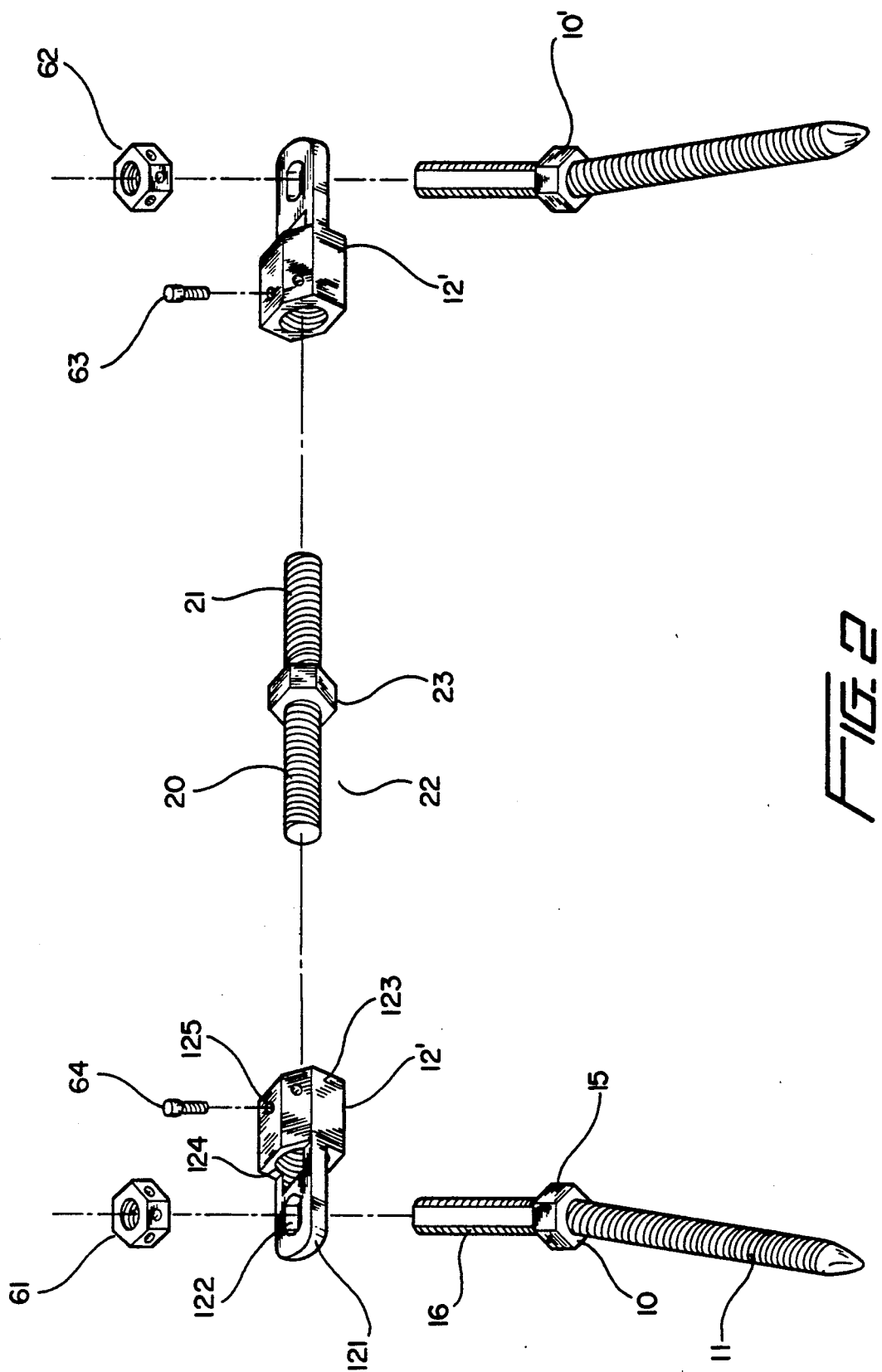
FIG. 2 shows an exploded perspective view of a vertebral locking and retrieving system constructed according to another preferred embodiment of the present invention.

A second preferred embodiment of the present invention is illustrated in FIG. 2 wherein like numerals are used to designate elements corresponding to the above described embodiment. The vertebra locking and retrieving system constructed according to this second embodiment comprises two locking pins 10, 10', two connectors 12, 12' one threaded rod 20 as the coupling component and two nuts 61, 62. The locking pin 10 is similar to that described in the prior embodiment except that the locking end 16 and the threaded end 11 form a specified angle. The connector 12 is also similar to that described in the prior embodiment, however, the plate 121 can be formed either at an acute angle of deflection or 0° of deflection relative to a longitudinal axis defined by the internally threaded bore 124. The assembly of the locking pin 10, the connector 12, the nut 61 and the left-handed thread 22 of the threaded rod 20 is analogous to that described in the prior embodiment. Symmetrically to the locking pin 10, the connector 12 and the nut 61 on the opposite side of a central dividing plane along the transverse direction of the polygonal drive portion 23, the locking pin 10', the connector 12' and the nut 62 are being assembled and mounted on the right-handed thread 21 of the threaded rod 20.

A similar vertebral locking and retrieving system which is useful in restoring a deformed vertebra of the lumber vertebrae is disclosed in the FIGS. 4(a)-4(c) of the present inventor's U.S. Pat. No. 5,196,014, the disclosure of which is incorporated herein by reference.

Figure 3:
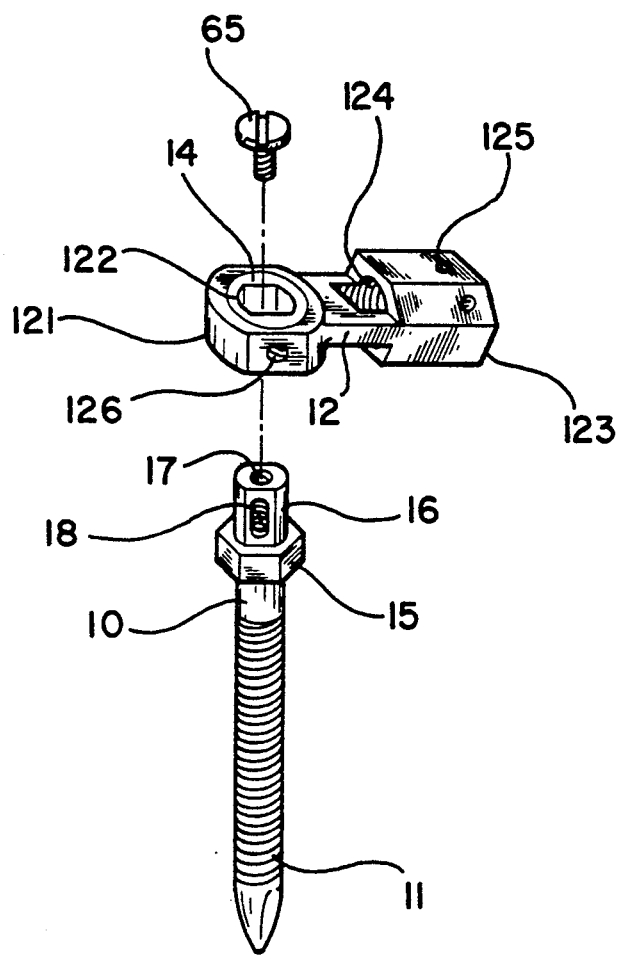
FIG. 3 shows an exploded perspective view of a connector, a locking pin and a locking bolt to be used in a locking and retrieving system constructed according to a third preferred embodiment of the present invention.

Referring to FIG. 3, a connector 12, a locking pin 10 and a locking bolt 65 to be used in a locking and retrieving system constructed according to a third preferred embodiment of the present invention are shown. The locking pin 10 has a threaded end 11 at its lower end, a rectangular or similar shaped post 16 at its upper end having a threaded bore 17 which is formed axially at the center thereof, and a stopping protrusion near the post 16. Preferably, a through hole 18 is provided on one of lateral sides of the post 16. The connector 12 includes a receiver part 123 at one end thereof and an integrally formed plate 121 at the other end thereof. The receiver part 123 has an internally threaded bore 124, and the plate 121 has an aperture 122 adapted to non-rotatably accept the post 16 such that the plate 121 rests on the stopping protrusion 15 to prevent movement of the plate 121 towards the vertebra. The plate 121 further has a recess 14 on the upper side about the aperture 122 and preferably a screw hole 126 on one of its lateral side. The locking bolt 65, after the aperture 122 non-rotatably receives the post 16 is then threaded into the threaded bore 17 with its head sinking into the recess 14 to fix the plate 121 onto the post 16 of the locking pin 10. Preferably, an additional reinforcing screw (not shown) may be provided to secure the engagement between the locking pin 10 and the connector 12 by tightening the reinforcing screw into the screw hole 126 of the plate and the through hole 18 of the post 16 and against the bolt 65. Similarly, the plate 121 of the connector 12 is formed at an acute angle of deflection relative to a longitudinal axis defined by the internally threaded bore 124, as the connector 12 shown in FIGS. 1 and 1(a).

It is obvious that the locking pin 10, the connector 12 and the locking bolt 65 described in the present FIG. 3 can be used in the system described in the present FIG. 1 or 2, therefore detailes thereof are omitted.

A fourth preferred embodiment of the present invention is illustrated in FIG. 4 wherein like numerals are used to designate elements corresponding to the above described embodiments. The locking pin 10, which is composed of a threaded end 11, a locking post 16, and a stopping protrusion 15, is again used to secure the vertebrae immediately adjacent to the deformed vertebra. The locking pin 10 is similar in structure to the one shown in FIG. 3 except that an externally threaded portion 127 is provided to replace the internally threaded bore 124. A connecting block 30 is provided with an 8-shape through hole 32 and threaded bores 31 and 31' (not shown). A threaded stud 20 having a threaded portion 25 at one end thereof and an internally threaded bore 24 formed axially at the center of the other end thereof is used to connect the connector 12 with the block 30, in which the externally threaded portion 127 of the connector 12 is threadably received within the internally threaded bore 24 of the threaded stud 20, and the threaded portion 25 of the threaded stud 20 is threadably received within the threaded bore 31 of the block 30. The remedial screw 40 is intended to remedy the deformed vertebra and is similar in structure to the one shown in FIG. 1. In this embodiment, however, two locking pin 10 and two threaded studs 20 are fastened together to form an unitary body. The two threaded studs 20 and the connecting block 30 are fixedly secured together by threading nuts 54 and 55 against the block 30. In the meantime, the nuts 56 are used to couple the block 30 with the remedial screw 40 with the 8-shaped through hole 32 permitting a slight adjustment of remedial screw 40 relative to the axis defined by threaded studs 20. The fastening block 30 and/or the threaded studs 20 can be constructed with a specific angle for enabling the system to cooperate with the curvature of the deformed vertebra.

A fifth preferred embodiment of the present invention is illustrated in FIG. 5 And FIG. 5(a) wherein like numerals are used to designate elements corresponding to the above described embodiments. The vertebra locking and retrieving system constructed according to this fifth embodiment is similar to that described in the first embodiment shown in FIG. 1 except that a regular threaded rod 20, a pair of nuts 50, 51 and a through hole 124a are provided in FIG. 5 to replace the threaded rod 20 and the internally threaded bore 124 in FIG. 1, and the locking pin 10 is connected to the connector 12 at a location lateral to the through hole 124a in FIG. 5 instead of a location in front of one opening of the threaded bore 124 in FIG. 1. Referring to FIG. 5 and 5(a), the connector 12 includes a receiver part 123 having a through hole 124a, and an integrally formed cubic portion 121 at one side of the through hole 124a having an aperture 122 adapted to non-rotatably accept the locking end 16 of the locking pin 10 such that the cubic portion 121 rests on the stopping protrusion 15 of the locking pin 10 to prevent movement of the cubic portion 121 towards the vertebra. The nut 61 is then engaged with the locking end 16 to fix the cubic portion 121 onto the locking end 16 of the locking pin 10. As shown in FIG. 5(a), the cubic portion 121 of the connector 12 is formed with a longitudinal axis 129 defined by the hole 122 at an acute angle of deflection relative to a plane 130 extending perpendicular to a longitudinal axis defined by the through hole 124a [not shown in FIG. 5(a)]of the connector 12.

The nuts 50 and 51 are used to fixedly attach the connector 12 to the threaded rod 20, wherein the nuts 50, 51 are mounted on the threaded rod 20 and driven to sandwich the receiver part 123 when the threaded rod 20 extends through the through hole 124a of the connector 12.

Based on the above discussion, it can readily be seen that the vertebral locking and retrieving system of the present invention is characterized in that it comprises locking pins, connectors, threaded rods, and nuts, all of which can be selectively employed in accordance with the position of the deformed vertebra, the symptoms of the deformed vertebra and the surgical requirements. For example, if the deformed vertebra happens to be the fourth vertebra of the lumbar vertebrae, the vertebral locking and retrieving systems of the present invention shown in FIGS. 1 and 5 functions effectively. In such a case, one threaded rod with the connecting block serves as the coupling component while a threaded screw is used as the remedial component. In addition, a plurality of nuts are used to work as locking and securing components (see FIGS. 1 and its corresponding text). In treating some slipped lumbar vertebrae, two threaded rods or studs united by one connecting block are used as the coupling component for two locking pins/connectors and one threaded screw as in the FIG. 4 embodiment. In the case of vertebral fracture or camel back, one threaded rod may be used to serve as the coupling component to interconnect two locking pins/connectors, one of which is used to work as a remedial component (see FIG. 2 and the corresponding text). Moreover, the locking pin and connector used in these surgical operation permits the surgeon to have a chance to amend the locking angle by choosing a connector having a different deflection angle if the locking pin secured to the vertebra should deflect from its planned angle.

In order to achieve a better surgical treatment, the present invention can also be employed in conjunction with numerous bone reinforcing devices known in the prior art, such as a cross bridging system.

Therefore, it can readily be seen that the present invention is characterized in that it comprises at least one locking pin and at least one connector either one or both of which are designed with a specified angle enabling the vertebral locking and retrieving system to cooperate with the specific curvature of the deformed vertebra under treatment, and that its various components can be used in different combinations on the basis of the surgical requirements and the symptom of the deformed vertebra under treatment. Furthermore, the present invention serves to simplify the surgical operation in such ways that it does not require of a surgeon to make a large incision, thereby minimizing the risk of an excessive bleeding by the patient receiving treatment; the patient's ability to move about is not seriously compromised by the surgical operation; and the patient's nervous system is less vulnerable to the pressure exerted thereon by the implanted system.

The embodiments of the present invention described above are to be considered in all respects as merely illustrations of principles of the present invention. Accordingly, the present invention is to be limited only by the scope of the following claims.

I claim:

1. A vertebral locking and retrieving system for use in retrieving a deformed vertebra and maintaining the deformed vertebra in a normal, healthy position comprising:

at least one locking pin having a threaded end portion adapted to be secured to a normal, healthy vertebra, an integrally formed locking end portion, and a stopping protrusion located between the threaded end portion and the locking end portion;

at least one connector comprising a receiver part having a cylindrical through hole defining a first longitudinal axis, and an integrally formed substantially cubic portion at one lateral side of said through hole, said cubic portion having a locking aperture adapted to non-rotatably accept the locking end portion of the at least locking pin such that the cubic portion rests on the stopping protrusion to prevent movement of the cubic portion towards the normal, healthy vertebra;

at least one locking component engageable with the locking end portion of said at least one locking pin after the locking end portion has passed through the locking aperture of the cubic portion to hold said at least one connector onto the at least one locking pin;

a remedial component adapted to be secured at one end thereof to one of a deformed vertebra located immediately adjacent to said normal, healthy vertebra but different from said normal, healthy vertebra to which said at least one locking pin is secured;

coupling means for interconnecting said at least one connector and said remedial component, said coupling means extending along said first longitudinal axis into said through hole of said receiver part and being threadably attached to said receiver part;

fastening means for fixedly securing said remedial component to said coupling means;

wherein said locking aperture of the substantially cubic portion of said at least one connector defines a second longitudinal axis that extends at an acute angle of deflection relative to a plane extending perpendicular to said first longitudinal axis.

2. A vertebral locking and retrieving system as claimed in claim 1, wherein said coupling means includes a rod having first and second threaded ends, the first end of said rod is passed through said through hole of said receiver part, and a pair of nuts are provided to threadably attached to said rod on the opposite sides of said receiver part.

3. A vertebral locking and retrieving system as claimed in claim 2, wherein the locking end portion of said locking pin is a polygon shaped post having a threaded end, the substantially cubic portion of said connector has a corresponding aperture to non-rotatably accept the post, and said at least one locking component is a nut threadably engageable with the post of the locking end.

4. A vertebral locking and retrieving system as claimed in claim 2, wherein said one end of said remedial component is threaded and the other end of said remedial component is connected to said coupling means.

5. A vertebral locking and retrieving system as claimed in claim 4, wherein said coupling means further includes an block, in which said second threaded ends of said rod is fixedly secured to said said block, and the other end of said remedial component is fixedly secured to said block.

6. A vertebral locking and retrieving system as claimed in claim 5, wherein said remedial component includes a stop member formed intermediate the ends thereof, said block includes a hole through which the other end of said remedial component projects such that said block engages said stop member when said remedial component is fixedly secured to said block.

7. A vertebral locking and retrieving system as claimed in claim 6, wherein the other end of said remedial component is threaded and said fastening means comprises at least one nut which is threadably received on said other end of said remedial component such that said block is sandwiched between said at least one nut and said stop member.

8. A vertebral locking and retrieving system as claimed in claim 1, wherein the locking end portion of said at least one locking pin is formed at an acute angle of deflection relative to a third longitudinal axis defined by said threaded end portion of said at least one locking pin.

* * * * *